US00PP22759P2

(12) United States Plant Patent
Bradford

(10) Patent No.: US PP22,759 P2
(45) Date of Patent: May 29, 2012

(54) NECTARINE TREE NAMED 'PEARLICIOUS II'

(50) Latin Name: *Prunus persica*
Varietal Denomination: Pearlicious II

(76) Inventor: Lowell Glen Bradford, Le Grand, CA (US)

( * ) Notice: Subject to any disclaimer, the term of this patent is extended or adjusted under 35 U.S.C. 154(b) by 9 days.

(21) Appl. No.: 12/928,441

(22) Filed: Dec. 13, 2010

(51) Int. Cl.
*A01H 5/00* (2006.01)

(52) U.S. Cl. ..... Plt./188

(58) Field of Classification Search ..... Plt./188
See application file for complete search history.

(56) References Cited

U.S. PATENT DOCUMENTS

PP7,421 P 1/1991 Bradford
PP18,706 P2 4/2008 Bradford

*Primary Examiner* — Susan McCormick Ewoldt

(57) ABSTRACT

The present invention relates to a new and distinct variety of nectarine tree, *Prunus persica*, broadly characterized by a large size, vigorous, half-hardy, self-fertile, very productive and regular bearing tree. The variety blooms between the early and mid season and requires about 500 chilling hours. The fruit matures under the ecological conditions described in early June, with first picking on Jun. 8, 2010. The fruit is uniformly large in size for an early season variety, a sub-acidic in flavor, globose to slightly oblong in shape, clingstone in type, firm and melting in texture, white in flesh color, and mostly red in skin color.

1 Drawing Sheet

Botanical classification: *Prunus persica.*
Variety denomination: 'Pearlicious II'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Pearlicious II'.

The present variety was hybridized by me in 2001 as a first generation cross using 'Rose Diamond' (U.S. Plant Pat. No. 7,421) nectarine as the selected seed parent and an unnamed white flesh nectarine seedling (unpatented) as the selected pollen parent. The fruit of this cross was gathered in the spring of 2001, and the seeds were removed from the fruit, germinated using an embryo rescue technique, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2005 I selected the present variety as a single tree from the group of seedlings described above. After its initial selection in 2005, the present variety was carefully observed and further evaluated during each subsequent fruiting season. As part of this testing process, I asexually reproduced the present variety by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Rose Diamond' nectarine by requiring about 500 chilling hours and by producing nectarines that are mostly red in skin color, clingstone in type, and firm in texture, but is distinguished therefrom by producing fruit that is white instead of yellow in flesh color, that is sub-acidic instead of acidic in flavor, and that matures about four days later.

The present variety is most similar to 'Pearlicious III' (U.S. Plant Pat. No. 18,706) nectarine by producing nectarines that are white in flesh color, clingstone in type, firm in texture, and sub-acidic in flavor, but is distinguished therefrom by requiring less chilling hours, by having a bitter instead of sweet kernel, and by producing fruit that is clingstone instead of freestone in type and that matures about seven days earlier.

SUMMARY OF VARIETY

In summary, the present nectarine variety is characterized by a large size, vigorous, half-hardy, self-fertile, very productive and regular bearing tree. The variety blooms between the early and mid season and requires about 500 chilling hours. The fruit matures under the ecological conditions described in early June, with first picking on Jun. 8, 2010. The fruit is uniformly large in size for an early season variety, a sub-acidic in flavor, globose to slightly oblong in shape, clingstone in type, firm and melting in texture, white in flesh color, and mostly red in skin color.

DRAWING

The accompanying photograph consists of four whole fruits positioned to display the characteristics of the skin color and form, two half fruits sectioned to reveal the flesh and stone, three insets to reveal buds and a blossoms, characteristic leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 14, 2010, on the original tree during its ninth growing season. The blossom and flower descriptions were made the previous blooming season. All major color code designations are by reference to the Inter-Society Color Council, National Bureau of Standards. Common color names are also used occasionally.

It is to be noted that the climatic conditions in 2010 led to delayed blooming and delayed fruit ripening for most of the season by approximately ten days. This should be taken into account when comparing to other variety descriptions made referencing different years. However, the relative blooming times and ripening times cited in this application are accurate for 2010, and should remain about the same in future years.

Parentage

Seed parent: 'Rose Diamond' nectarine (U.S. Plant Pat. No. 7,421).

Pollen parent: Unnamed white flesh nectarine (unpatented).

Tree

Size: Large, reaching and maintaining a height of 12' [3.66 m.] and a spread of 12' [3.66 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Half-hardy with respect to central California winters.

Approximate chilling requirement: 500 hours.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

*Size*.—Medium, reaching a maximum diameter of 8" [203.2 mm.] after the ninth growing season.

*Texture*.—Shaggy.

*Bark color*.—A Dark grayish reddish brown [47. d.gy.rBr] and Dark grayish brown [62. d.gy.Br] variegation with Moderate yellowish brown [77. m.yBr] crevices present.

*Lenticels*.—Approximate Number Per Square Inch: 8. Color: Dark orange yellow [72. d.OY]. Average Size: 7/16" [11.1 mm.]. Shape: Eye-shaped, elongated.

Branches:

*Size*.—Diameter of limb is 4⅛" [104.8 mm.] measured 12" above the crotch, 2½" [63.5 mm.] measured 12" above the first fork.

*Texture*.—Smooth on first year wood, increasing roughness with age.

*Color*.—1st Year Wood Topside: Grayish red [19. gy.R]. 1st Year Wood Underside: Brilliant yellow green [116. brill.YG]. Second Year Wood: Deep yellowish brown [75. deep yBr]. Older Wood: A Dark brown [59. d.Br] and Dark grayish brown [62. d.gy.Br] variegation.

*Lenticels*.—Number Per Square Inch: About 100 on second year wood. Color: Light yellowish brown [76. l.yBr]. Average size: 1/32" [0.8 mm.] to 3/32" [2.4 mm] on second year wood. Shape: Eye-shaped, elongated.

Leaves:

*Size*.—Medium. Average Length: 5⅜" [136.5 mm.]. Average Width: 1 9/16" [39.7 mm.].

*Arrangement*.—Alternate.

*Thickness*.—Medium.

*Form*.—Elliptical.

*Apex*.—Acuminate.

*Base*.—Acute, with an average base angle of 75 degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Light yellow green [119. l.YG].

*Petiole*.—Average Length: ⅜" [9.5 mm.]. Average Thickness: 3/32" [2.4 mm.]. Color: Deep yellow green [118. deep YG].

*Stipules*.—Number: Usually 2 per leaf, up to 6 per growing tip. Average Length: 5/16" [7.9 mm.]. Color: Light yellow green [119. l.YG] becoming Light olive brown [94. l.olBr] with maturity.

*Glands*.—Number: 2 to 4 per leaf. Position: Alternate. Size: Small. Form: Globose. Color: Light yellow green [119. l.YG] becoming Grayish reddish brown [46. gy.rBr] with age.

*Leaf buds*.—Pointed, medium in size.

Flower buds:

*Hardiness*.—Half-hardy, with respect to central California winters.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.

*Tip color*.—Light purplish pink [249. l.pPk].

Flowers: Perfect, complete, perigynous, usually a single pistil, about thirty stamens, five sepal and petal locations alternately positioned.

*Type*.—Showy, large.

*Average flower diameter*.—2" [50.8 mm.].

*Number of petals*.—Mostly five, but about thirty percent have extra petal fragments or double blossoms.

*Petal shape*.—Circular to oval.

*Petal margin*.—Entire, slightly wavy.

*Average petal diameter*.—¾" [19.1 mm.].

*Average petal length*.—13/16" [20.6 mm.].

*Petal apex*.—Rounded.

*Petal base*.—Rounded to somewhat truncate.

*Petal color*.—Pale purplish pink [252. p.pPk] on both sides over most of the surface, Strong purplish pink [247. s.pPk] toward the base on some.

*Anther color*.—Strong red [12. s.R] over a Light yellow [86. l.Y] center at bloom onset.

*Stigma color*.—Pale yellow green [121. p.YG].

*Sepal color*.—Dark purplish red [259. d.pR] on the outer surface.
*Sepal length*.—5/16" [7.9 mm.].
*Sepal width*.—3/16" [4.8 mm.].
*Sepal apex*.—Rounded to elliptical to match the sepal length and width.
*Sepal margin*.—Fairly smooth.
*Average pistil length*.—3/4" [19.1 mm.].
*Average stamen length*.—9/16" [14.3 mm.].
*Fragrance*.—Moderate.
*Blooming period*.—Early to mid season, with 'Rose Diamond' (U.S. Plant Pat. No. 7,421) nectarine.
*Onset of bloom*.—One percent on Feb. 16, 2010.
*Date of full bloom*.—Feb. 23, 2009.
*Duration of bloom*.—One to two weeks, dependent on ambient temperature.
*Number per cluster*.—1 to 3 with single flowers most common.

Fruit

Maturity when described: Firm ripe, Jun. 14, 2010.
Date of first picking: Jun. 8, 2010.
Date of last picking: Jun. 20, 2010.
Size: Uniform, large.
*Average diameter axially*.—3" [76.2 mm.].
*Average diameter across cheek plane*.—2 13/16" [71.5 mm.].
*Average diameter across suture plane*.—2 13/16" [71.5 mm.].
*Typical weight*.—6.5 ounces [184.27 grams].
Form: Uniform, globose to slightly oblong.
*Longitudinal section form*.—Oblong to somewhat oval.
*Transverse section through diameter*.—Round.
Suture: Extends from the base, along the side, just to the pistil point.
*Near the base*.—A shallow groove becoming sharp very near the stem.
*Along the side*.—A shallow trough.
*Near the apex*.—A shallow groove.
Ventral surface: Rounded, lipped on both sides stronger toward the apex.
Lips: Equal.
Cavity: Flaring, circular, suture showing on one side, Light orange yellow [70. l.OY] stem markings typical.
*Depth*.—7/16" [11.1 mm.].
*Breadth*.—7/8" [22.2 mm.].
Base: Truncate, slightly cordate if viewed parallel to the suture.
Apex: Rounded, about five percent slightly mammiform.
Pistil point: Apical, typically 1/16" [1.6 mm.] in length, usually depressed within the suture with about five percent protruding.
Stem: Medium.
*Average length*.—7/16" [11.1 mm.].
*Average width*.—3/16" [4.8 mm.].
Skin:
*Thickness*.—Medium.
*Surface*.—Smooth.
*Tenacity*.—Tenacious to flesh.
*Astringency*.—Nonastringent.
*Tendency to crack*.—None observed in dry seasons, slight in wet seasons.
*Color*.—Dark red [16. d.R] over a Very red [11. v.R] background with Pale orange yellow [73. p.OY] freckling on the sides and stronger toward the apex.
Flesh:
*Color*.—Greenish white [153. gWhite].
*Surface of pit cavity*.—Covered with Yellowish white [92. yWhite] broken fibers when twisted from the stone.
*Amygdalin*.—Scarce.
*Juice*.—Moderate, rich.
*Texture*.—Firm, tough, meaty.
*Fibers*.—Few, fine, tender.
*Ripens*.—Fairly evenly, slightly earlier at the apex.
*Flavor*.—Subacid and sweet, typically 16 to 20 brix.
*Aroma*.—Wanting.
*Eating quality*.—Very good.

Stone

Type: Freestone.
Form: Obovate.
Hilum: Narrow, oblong.
Base: Rounded.
Apex: Acuminate with a small, sharp 1/8" [3.2 mm.] tip.
Sides: Fairly equal.
Surface: Irregularly furrowed toward the apex, pitted toward the base.
Ridges: Jagged.
External color: Light orange yellow [70. l.OY].
Pit wall color when cracked: Pale orange yellowish [73. p.OY].
Cavity surface color: Light yellowish brown [76. l.yBr].
Average pit wall thickness: 3/16" [4.8 mm.].
Average width: 1 1/16" [27 mm.].
Average length: 1 5/8" [41.3 mm.].
Average breadth: 3/4" [19.1 mm.].
Tendency to split: None observed.
Kernel:
*Form*.—Oval.
*Skin color*.—Pale greenish yellow [104. p.gY] when first removed.
*Pellicle color*.—Light gray [264. l.Gy].
*Vein color*.—Light greenish yellow [101. l.gY].
*Taste*.—Bitter.
*Viable*.—Yes, using embryo-culture techniques.
*Average width*.—1/2" [12.7 mm.].
*Average length*.—3/4" [19.1 mm.].
*Amygdalin*.—Abundant.

Use

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to 'Pearlicious III' (U.S. Plant Pat. No. 18,706) nectarine by producing nectarines that are white in flesh color, clingstone in type, firm in texture, and sub-acidic in flavor, but is distinguished therefrom by requiring less chilling hours, by having a bitter instead of sweet kernel, and by producing fruit that is clingstone instead of freestone in type and that matures about seven days earlier.

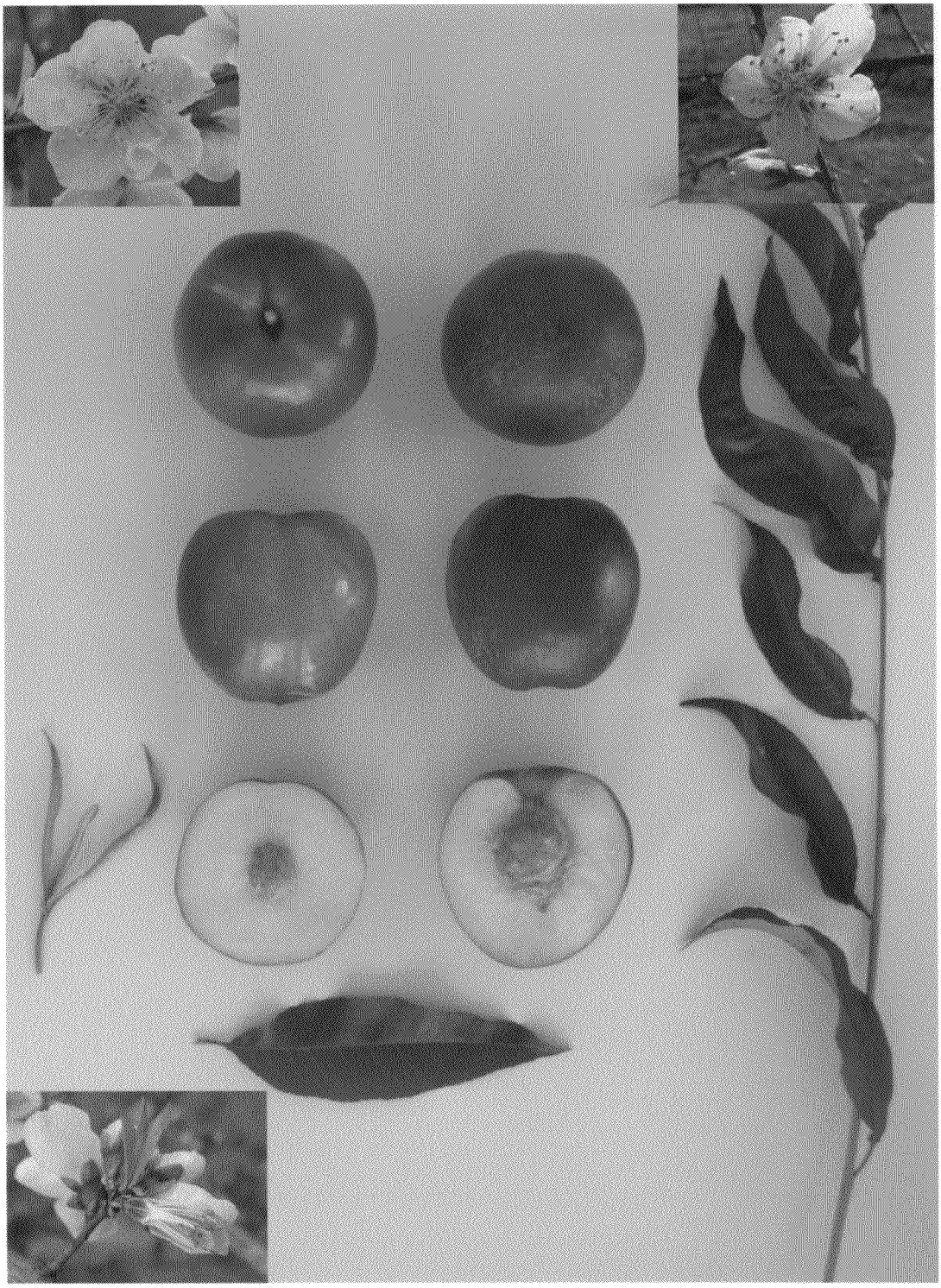

* * * * *